(12) United States Patent
Smith

(10) Patent No.: US 11,484,491 B1
(45) Date of Patent: Nov. 1, 2022

(54) SHAMPOO COMPOSITION

(71) Applicant: HauteHerbotique, LLC, Evanston, IL (US)

(72) Inventor: Marlene M. Smith, Evanston, IL (US)

(73) Assignee: HauteHerboutique, LLC, Evanston, IL (US)

( * ) Notice: Subject to any disclaimer, the term of this patent is extended or adjusted under 35 U.S.C. 154(b) by 585 days.

(21) Appl. No.: 16/393,229

(22) Filed: Apr. 24, 2019

(51) Int. Cl.
| A61K 8/98 | (2006.01) |
| A61K 8/19 | (2006.01) |
| A61K 8/9789 | (2017.01) |
| A61Q 5/02 | (2006.01) |
| A61K 8/365 | (2006.01) |

(52) U.S. Cl.
CPC .............. *A61K 8/986* (2013.01); *A61K 8/19* (2013.01); *A61K 8/365* (2013.01); *A61K 8/9789* (2017.08); *A61K 8/988* (2013.01); *A61Q 5/02* (2013.01); *A61K 2800/5922* (2013.01)

(58) Field of Classification Search
None
See application file for complete search history.

(56) References Cited

U.S. PATENT DOCUMENTS

2009/0130220 A1* 5/2009 Johnson ................ A61K 8/645
424/539

FOREIGN PATENT DOCUMENTS

| CN | 106038388 A | * | 10/2016 | |
| WO | WO-2015148523 A1 | * | 10/2015 | ........... A61K 8/9794 |

OTHER PUBLICATIONS

Anna. Nature Helps Me "Mustard Benefits for Hair Growth" < https://naturehelps.me/hair-care/effective-mask-hair-growth> Jun. 28, 2015; accessed Sep. 20, 2021 (Year: 2015).*
Surabhi Saxena. Hibiscus Powder for Hair Growth: Benefits, Ways, to Use & Expert Tips. < https://cashkaro.com/blog/hibiscus-powder-for-hair-growth-benefits-ways-to-use-expert-tips/57436> Aug. 16, 2018; accessed Sep. 20, 2021 (Year: 2018).*

* cited by examiner

*Primary Examiner* — Nicole P Babson
(74) *Attorney, Agent, or Firm* — Fay Sharpe LLP

(57) ABSTRACT

The present disclosure relates to shampoo compositions comprising (A) either egg yolk powder or baking soda, (B) honey powder, (C) goat milk powder, and (D) water. Additional ingredients may also be present in the shampoo compositions. Such compositions provide improved characteristics such as fewer tangles, less shampoo residue post-use, and improved ability to work in tandem with other hair products.

13 Claims, No Drawings

SHAMPOO COMPOSITION

BACKGROUND

The present disclosure relates to compositions for use as shampoo.

Shampoo compositions to be used on the hair of a human being or the fur of a pet vary with respect to their properties, including ease of wet combing, presence of tangles or residue post-use, and ability to work in conjunction with other hair products. It is desirable to produce a shampoo composition that exhibits characteristics such as ease of use, absence of residue, and effective concurrent use with other products.

BRIEF DESCRIPTION

Disclosed, in various embodiments, are organic shampoo compositions which provide desirable qualities to hair after being used. It is contemplated that such shampoo compositions can be used on both humans or pets (e.g. cats, dogs, or other animals).

In embodiments, the shampoo composition comprises (A) either egg yolk powder or baking soda, (B) honey powder, and (C) goat milk powder in dry form. This dry powder mixture can be mixed with (D) water to obtain a shampoo.

In various embodiments, the shampoo composition can also include combinations of white vinegar powder, hibiscus powder, mustard seed powder, dry citric acid, a moisturizer, a fragrance, and/or an emulsifier. Several specific combinations of these additional ingredients are described herein.

Disclosed in various embodiments herein are shampoo compositions, comprising: either egg yolk powder or baking soda; honey powder; and goat milk powder.

In particular embodiments, the composition comprises egg yolk powder. The volume ratio of egg yolk powder to honey powder may be from about 12:1 to about 8:2. The volume ratio of egg yolk powder to goat milk powder may be from about 12:2 to about 8:4. The volume ratio of honey powder to goat milk powder may be from about 1:3 to about 2:2.

In additional embodiments, the composition may further comprise white vinegar powder. The egg yolk powder, white vinegar powder, honey powder, and goat milk powder may be present in a volume ratio of about 8:1:1:2. The volume ratio of egg yolk powder to white vinegar powder may be from about 12:1 to about 8:2. The volume ratio of white vinegar powder to honey powder may be from about 1:2 to about 2:1. The volume ratio of white vinegar powder to goat milk powder may be from about 1:3 to about 2:2.

In other embodiments, the composition may comprise both egg yolk powder and baking soda. The volume ratio of egg yolk powder to baking soda may be from about 8:72 to about 12:48.

In further embodiments, the composition may further comprise mustard seed powder. The volume ratio of mustard seed powder to egg yolk powder may be from about 2:8 to about 1:12. The volume ratio of mustard seed powder to baking soda may be from about 2:48 to about 1:72. The volume ratio of mustard seed powder to honey powder may be from about 2:1 to about 1:2. The volume ratio of mustard seed powder to goat milk powder may be from about 1:3 to about 2:2.

In some embodiments, the composition can further comprise mustard seed powder and hibiscus powder. The volume ratio of mustard seed powder to hibiscus powder may be from about 2:1 to about 1:2.

In other embodiments, the composition can further comprise mustard seed powder and dry citric acid. The volume ratio of mustard seed powder to dry citric acid may be from about 2:1 to about 1:2.

In yet more specific embodiments, the composition further comprises mustard seed powder, hibiscus powder, and dry citric acid. The mustard seed powder, hibiscus powder, and dry citric acid may be present in ratios of about 1:1:1.

In specific embodiments, the composition comprises egg yolk powder, honey powder, goat milk powder, baking soda, hibiscus powder, mustard seed powder, and dry citric acid. The egg yolk powder, honey powder, goat milk powder, baking soda, hibiscus powder, mustard seed powder, and dry citric acid may be present in a volume ratio of about 8:1:2:48:1:1:1.

In other specific embodiments, the composition comprises egg yolk powder, honey powder, goat milk powder, baking soda, hibiscus powder, and mustard seed powder. The egg yolk powder, honey powder, goat milk powder, baking soda, hibiscus powder, and mustard seed powder may be present in a volume ratio of about 8:1:2:48:1:1:1.

In additional specific embodiments, the composition comprises egg yolk powder, honey powder, goat milk powder, baking soda, mustard seed powder, and dry citric acid. The egg yolk powder, honey powder, goat milk powder, baking soda, mustard seed powder, and dry citric acid may be present in a volume ratio of about 8:1:2:48:1:1:1.

The composition may further comprise a moisturizer. Examples of moisturizers include methi powder, neem powder, or aloe powder. The composition may further comprise a fragrance. Examples of fragrance include rose, geranium, chamomile, or lavender. The composition may further comprise an emulsifier. Examples of emulsifier include guar gum or agar or filé powder.

The composition may further comprise water. A desirable pH of such compositions is from about 5.0 to about 7.0.

Also disclosed herein in various embodiments are methods for making a composition, comprising combining (A) either egg yolk powder or baking soda, (B) honey powder, and (C) goat milk powder to form a powder mixture.

The methods disclosed herein may further comprise combining white vinegar powder, and/or mustard seed powder, and/or hibiscus powder, and/or dry citric acid, and/or a moisturizer, and/or a fragrance, and/or an emulsifier into the powder mixture, in any combination of these ingredients.

The powder mixture can be further mixed with water.

These and other non-limiting characteristics are more particularly described below.

DETAILED DESCRIPTION

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named ingredients and permit the presence of other ingredients. However, such description should be construed as also describing compositions or processes as "consisting of" and "consisting essentially of" the enumerated ingredients, which allows the presence of only the named ingredients, along with any unavoidable impurities that might result therefrom, and excludes other ingredients.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number.

The present disclosure relates to shampoo compositions. The compositions can be provided in dry form (i.e. as a mixture of powders) or in a wet form. The components of the shampoo compositions of the present disclosure are very generally (A) an emulsifier or baking soda, (B) a moisturizing agent, and (C) milk powder. In additional embodiments, the components of the shampoo compositions of the present disclosure are an emulsifier, a moisturizing agent, milk powder, and water. In some specific embodiments, a pH buffer is also present.

Suitable emulsifiers include egg yolk, egg yolk powder, and similar compounds known in the art. The emulsifier provides oil and moisture to the shampoo composition. Baking soda, or sodium bicarbonate ($NaHCO_3$) is useful for removing dirt and buildup from the scalp. The emulsifier or baking soda is the majority of the shampoo composition by volume.

A suitable moisturizing agent is honey or honey powder. This affects wetting and absorption.

A suitable milk powder is goat milk powder. However, any milk that exhibits similar characteristics to goat milk, particularly with respect to the fat content, could be used.

When present, suitable pH buffers include white vinegar, white vinegar powder, and similar compounds known in the art. Desirably, the shampoo composition has a pH of about 6, including from about 5.0 to about 7.0. The pH buffer and the moisturizing agent may be present in approximately equal amounts. In some embodiments, the combined volume of the pH buffer and the moisturizing agent is approximately equal to the volume of the milk powder. In other embodiments, the combined volume of the pH buffer, the moisturizing agent, and the milk powder is approximately equal to half the volume of the emulsifier in the mixture.

In additional embodiments, the shampoo composition may include hibiscus powder, mustard seed powder, and/or dry citric acid. The mustard seed powder is believed to act as a wetting agent. The dry citric acid may be, for example, in the form of powder or crystals.

A moisturizer may also be present. Examples of moisturizers include methi powder, neem powder, and aloe powder.

A fragrance may also be present, for imparting a desirable scent to the shampoo composition. Such fragrances may include rose, geranium, chamomile, or lavender. These fragrances may be provided in the form of powders.

Additional emulsifier, such as guar gum or agar or filé powder, can also be present. Filé powder is made from dried and ground sassafras leaves.

When present, the weight ratio of moisturizer, fragrance, and/or additional emulsifier to the milk powder is usually up to about 2:4, including up to about 1:4. This weight ratio applies to each of these three ingredients separately. For example, if the milk powder is present in the amount of ¼ teaspoon, then the composition might contain moisturizer, fragrance, and additional emulsifier in an amount of ¹⁄₁₆ teaspoon (i.e. 1:4).

The volume ratio of egg yolk powder to honey powder may be from about 12:1 to about 8:2, including about 8:1.

The volume ratio of egg yolk powder to goat milk powder may be from about 12:2 to about 8:4, including about 8:2.

The volume ratio of honey powder to goat milk powder may be from about 1:3 to about 2:2, including about 1:2.

In some particular embodiments that include a pH buffer, the specific pH buffer can be white vinegar powder. The egg yolk powder, white vinegar powder, honey powder, and goat milk powder may be present in a volume ratio of about 8:1:1:2. More generally, the volume ratio of egg yolk powder to white vinegar powder can be from about 12:1 to about 8:2. The volume ratio of white vinegar powder to honey powder can be from about 1:2 to about 2:1. The volume ratio of white vinegar powder to goat milk powder can be from about 1:3 to about 2:2.

In some particular embodiments, the shampoo composition can comprise both an emulsifier (such as egg yolk powder) and baking soda. The volume ratio of emulsifier (egg yolk powder) to baking soda can be from about 8:72 to about 12:48.

When mustard seed powder is present, the volume ratio of mustard seed powder to egg yolk powder can be from about 2:8 to about 1:12. The volume ratio of mustard seed powder to baking soda may be from about 2:48 to about 1:72. The volume ratio of mustard seed powder to honey powder may be from about 2:1 to about 1:2. The volume ratio of mustard seed powder to goat milk powder may be from about 1:3 to about 2:2.

In some embodiments, both mustard seed powder and hibiscus powder are present in the shampoo composition. The volume ratio of mustard seed powder to hibiscus powder may be from about 2:1 to about 1:2.

In some embodiments, both mustard seed powder and dry citric acid are present in the shampoo composition. The volume ratio of mustard seed powder to dry citric acid may be from about 2:1 to about 1:2.

In some other embodiments, the shampoo composition further comprises mustard seed powder, hibiscus powder, and dry citric acid. The mustard seed powder, hibiscus powder, and dry citric acid can be present in ratios of about 1:1.

Any combination of these volume ratios for these ingredients is contemplated to be within the scope of this disclosure. The dry powder mixtures are believed to be long-term stable at room temperature.

In some specific examples, the shampoo composition comprises egg yolk powder, honey powder, goat milk powder, baking soda, hibiscus powder, mustard seed powder, and dry citric acid. The egg yolk powder, honey powder, goat milk powder, baking soda, hibiscus powder, mustard seed powder, and dry citric acid can be present in a volume ratio of about 8:1:2:48:1:1:1.

In other examples, the shampoo composition comprises egg yolk powder, honey powder, goat milk powder, baking soda, hibiscus powder, and mustard seed powder. The egg yolk powder, honey powder, goat milk powder, baking soda, hibiscus powder, and mustard seed powder can be present in a volume ratio of about 8:1:2:48:1:1.

In still other examples, the shampoo composition comprises egg yolk powder, honey powder, goat milk powder, baking soda, mustard seed powder, and dry citric acid. The egg yolk powder, honey powder, goat milk powder, baking soda, mustard seed powder, and dry citric acid may be present in a volume ratio of about 8:1:2:48:1:1:1.

The dry powder mixtures described herein may be combined with water to form an operative shampoo in any amount as desired by the user. In particular embodiments, about 3 teaspoons to about 9 teaspoons, including about 6 teaspoons (i.e. 2 tablespoons), of the dry powder mixture is mixed with about 2 cups of water. The pH of the liquid shampoo composition may be from about 5.0 to about 7.0, when about 6 teaspoons of the dry powder mixture is mixed with about 2 cups of water. In specific embodiments, the pH of the liquid composition may be about 6.0.

Although described above in terms of powder, the shampoo compositions can also be made by combining the wet forms of the various powders. It is believed that these liquid components would also be combined in the same volume ratios as discussed above. Any organic ingredients known in the art to preserve or improve stability of the resulting composition may also be used.

The following examples are provided to illustrate the shampoo compositions of the present disclosure. The examples are merely illustrative and are not intended to limit the disclosure to the materials, conditions, or process parameters set forth therein.

EXAMPLES

The following ingredients were mixed together to form a dry powder mixture: 1 teaspoon of egg yolk powder; ⅛ teaspoon of white vinegar powder; ⅛ teaspoon of honey powder; and ¼ teaspoon of goat milk powder. The dry powder mixture was then added to 2 cups of water and stirred.

The following ingredients were mixed together to form a dry powder mixture: 1 teaspoon of egg yolk powder; 2 tablespoons (6 teaspoons) of baking soda; ⅛ teaspoon of honey powder; ¼ teaspoon of goat milk powder; ⅛ teaspoon hibiscus powder; ⅛ teaspoon mustard seed powder; and ⅛ teaspoon citric acid powder.

The following ingredients were mixed together to form a dry powder mixture: 1 teaspoon of egg yolk powder; 2 tablespoons (6 teaspoons) of baking soda; ⅛ teaspoon of honey powder; ¼ teaspoon of goat milk powder; ⅛ teaspoon hibiscus powder; and ⅛ teaspoon mustard seed powder.

The following ingredients were mixed together to form a dry powder mixture: 2 tablespoons (6 teaspoons) of baking soda; ⅛ teaspoon of honey powder; ¼ teaspoon of goat milk powder; ⅛ teaspoon honey powder; ⅛ teaspoon mustard seed powder; and ⅛ teaspoon citric acid powder.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A dry shampoo composition, consisting of:
    egg yolk powder and baking soda;
    honey powder;
    goat milk powder;
    mustard seed powder;
    hibiscus powder; and
    dry citric acid;
    wherein a volume ratio of mustard seed powder to hibiscus powder is from about 2:1 to about 1:2; and
    wherein a volume ratio of mustard seed powder to dry citric acid is from about 2:1 to about 1:2; and
    optionally white vinegar powder, a moisturizer, a fragrance, or an emulsifier.

2. The composition of claim 1, wherein a volume ratio of egg yolk powder to honey powder is from about 12:1 to about 8:2.

3. The composition of claim 1, wherein a volume ratio of egg yolk powder to goat milk powder is from about 12:2 to about 8:4.

4. The composition of claim 1, wherein a volume ratio of honey powder to goat milk powder is from about 1:3 to about 2:2.

5. The composition of claim 1, further comprising white vinegar powder.

6. The composition of claim 1, wherein a volume ratio of mustard seed powder to honey powder is from about 2:1 to about 1:2; and
    wherein a volume ratio of mustard seed powder to goat milk powder is from about 1:3 to about 2:2.

7. The composition of claim 6, wherein the pH of the composition is from about 5.0 to about 7.0.

8. The composition of claim 1, wherein the moisturizer is methi powder, neem powder, or aloe powder.

9. The composition of claim 1, wherein the fragrance is rose powder, geranium powder, chamomile powder, or lavender powder.

10. The composition of claim 1, wherein the emulsifier is guar gum, agar, or filé powder.

11. A wet composition, consisting of:
    water;
    either egg yolk powder or baking soda;
    honey powder;
    goat milk powder;
    mustard seed powder;
    hibiscus powder; and
    dry citric acid;
    wherein a volume ratio of mustard seed powder to hibiscus powder is from about 2:1 to about 1:2; and
    wherein a volume ratio of mustard seed powder to dry citric acid is from about 2:1 to about 1:2; and
    optionally white vinegar powder, a moisturizer, a fragrance, or an emulsifier.

12. A method for making a composition, comprising forming a powder mixture consisting of (A) egg yolk powder and baking soda, (B) honey powder, (C) goat milk powder, (D) mustard seed powder, (E) hibiscus powder, and (F) dry citric acid, and (G) optionally white vinegar powder, a moisturizer, a fragrance, or an emulsifier;
    wherein a volume ratio of mustard seed powder to hibiscus powder is from about 2:1 to about 1:2; and
    wherein a volume ratio of mustard seed powder to dry citric acid is from about 2:1 to about 1:2.

13. The method of claim 12, wherein the powder mixture is mixed with water.

* * * * *